United States Patent [19]

Danvy et al.

[11] Patent Number: 6,013,829
[45] Date of Patent: Jan. 11, 2000

[54] PROCESS FOR THE ASYMMETRIC SYNTHESIS OF S-ACYL DERIVATIVES OF 2-MERCAPTOMETHYL -3- PHENYL PROPANOIC ACID, APPLICATION TO THE SYNTHESIS OF N-(MERCAPTOACYL) AMINO ACID DERIVATIVES

[75] Inventors: Denis Danvy, Yvetot; Thierry Monteil, Mont Saint Aignan; Pierre Duhamel, Mont Saint Aignan; Lucette Duhamel, Mont Saint Aignan; Jeanne-Marie Lecomte; Jean-Charles Schwartz, both of Paris; Nadine Noel-Lefebvre, Jouars Pontchartrin; Claude Gros, Paris; Jean-Christophe Plaquevent, Deville les Rouen, all of France

[73] Assignee: Societe Civile Bioprojet, France

[21] Appl. No.: 08/930,734

[22] PCT Filed: Feb. 4, 1997

[86] PCT No.: PCT/FR97/00218

§ 371 Date: Nov. 26, 1997

§ 102(e) Date: Nov. 26, 1997

[87] PCT Pub. No.: WO97/29086

PCT Pub. Date: Aug. 14, 1997

[30] Foreign Application Priority Data

Feb. 5, 1996 [FR] France ................... 96 01360

[51] Int. Cl.[7] ................ C07C 321/00; C12P 13/04
[52] U.S. Cl. ................ 560/16; 562/418; 562/426; 435/106; 435/128; 435/130
[58] Field of Search ................ 435/130, 128, 435/106; 562/418, 426; 560/16

[56] References Cited

FOREIGN PATENT DOCUMENTS

| 136883 | 4/1985 | European Pat. Off. . |
| 377139 | 7/1990 | European Pat. Off. . |
| 2623498 | 5/1989 | France . |
| 501870 | 9/1992 | France . |

OTHER PUBLICATIONS

Mori et al, "Preparation . . . Key Step", Liebigs Ann. Chem., No. 10, 1989 pp. 957962, XP 000611532.

Atsuumi et al, "An Efficient . . . Reaction", Tetrahedron Letters, vol. 31, No. 11, 1990, pp. 1601–1604, XP 002020256.

Strijiveen et al, "Evidence . . . Reagent", Recueil de Travaux Chimiques des Pays–Bas, vol. 106, No. 10, 1987, pp. 539–542 XP 000196631.

Caron et al, "Sequential . . . Cepacia", vol. 4, No. 9, 1993, pp. 1995–2000, XP000611535.

Primary Examiner—Samuel Barts
Attorney, Agent, or Firm—Bierman, Muserlian and Lucas

[57] ABSTRACT

Process for the asymmetric synthesis of S-acyl derivatives of 2-mercaptomethyl-3-phenylpropanoic acid of formula (I):

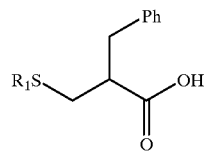

(I)

characterized in that it comprises the steps consisting in:

a) preparing the diol (VI) by reduction of a malonic ester (V) in the presence of a hydride;
b) preparing the monoacetates (VII R) or (VII S) respectively;
c) subjecting these monoacetates to an oxidation in order to form the acids (IX S) or (IX R);
d) saponifying the compounds (IX S) or (IX R) in order to form the hydroxy acids (X S) or (X R);
e) thioacylating the hydroxy acids (X S) or (X R) with a mercapto acid $R_1SH$ (XI), according to a Mitsunobu-type reaction, in order to lead to the desired acids (I R) (I S) respectively and application to the synthesis of N-(mercaptoacyl)amino acid derivatives (II).

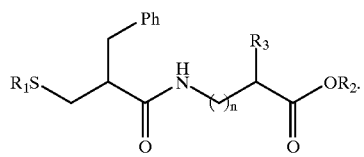

(II)

21 Claims, No Drawings

PROCESS FOR THE ASYMMETRIC SYNTHESIS OF S-ACYL DERIVATIVES OF 2-MERCAPTOMETHYL -3- PHENYL PROPANOIC ACID, APPLICATION TO THE SYNTHESIS OF N-(MERCAPTOACYL) AMINO ACID DERIVATIVES

This application is a 371 of PCT/FR97/00218 filed Feb. 4, 1997.

The present invention relates to a process for the enantioselective synthesis of S-acyl derivatives of 2-mercaptomethyl-3-phenylpropanoic acid and to their use in the asymmetric synthesis of N-(mercaptoacyl)-amino acid derivatives. More specifically, the present invention relates to a novel process for the synthesis of optically pure derivatives of general formula (I):

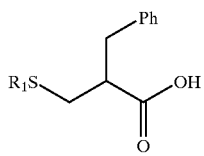
(I)

in which:

R$_1$ represents a linear or branched aliphatic acyl radical or an aromatic acyl radical.

The derivatives of formula (I) obtained according to the process of the invention are useful in particular for the synthesis of optically active N-(mercaptoacyl)amino acid derivatives of formula (II):

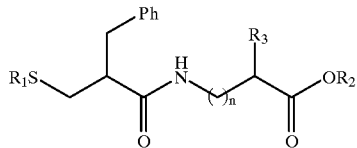
(II)

in which:

R$_1$ represents a hydrogen atom, a linear or branched aliphatic acyl radical or an aromatic acyl radical;

R$_2$ represents a hydrogen atom, a lower alkyl radical, a phenyl radical or a lower phenylalkylene group;

R$_3$ represents a hydrogen atom; a lower alkyl group; a lower hydroxyalkylene group; a phenyl group; a lower phenylalkylene group; a lower hydroxyphenylalkylene group; a lower aminoalkylene group; a lower guanidinoalkylene group; a lower mercaptoalkylene group; a lower alkyl lower thioalkylene group; a lower imidazolylalkylene group; a lower indolylalkylene group; a lower carbamylalkylene group; a lower carboxyalkylene group; n ranges from 0 to 10.

The expression lower alkyl group is understood to refer to alkyl groups having linear or branched chains containing from 1 to 6 carbon atoms and preferably 1 to 4 carbon atoms.

The expression lower alkylene group is understood to refer to alkylene groups containing from 1 to 6 carbon atoms and preferably 1 to 4 carbon atoms.

The preferred compounds of formula (II) are the compounds corresponding to formulae (III) and (IV) below:

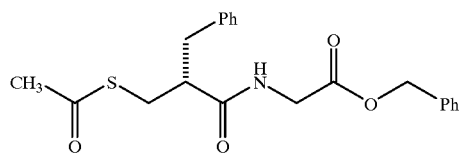
(III)

or benzyl N—(R)-[2-acetylthiomethyl-1-oxo-3-phenylpropyl]glycinate;

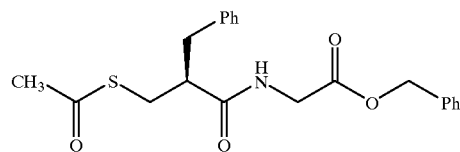
(IV)

or benzyl N—(S)-[2-acetylthiomethyl-1-oxo-3-phenylpropyl]glycinate, for which the process of the present invention may be applied more particularly.

The compounds of formula (II) have advantageous pharmacological properties. In particular, they exert an inhibitory activity on certain enzymes, such as neutral endopeptidase (EC 3.4.24.11) and the angiotensin conversion enzyme (EC 3.4.15.1). The administration of the compounds of formula (II) thus makes it possible to reduce or eliminate the activity of these enzymes, which are respectively responsible for the inactivation of encephalins, of atrial natriuretic factor, and for the conversion of angiotensin I into angiotensin II. In therapeutic treatment, these compounds exert antisecretory, intestinal or antihypertensive activities and are used in the treatment of chronic cardiac insufficiency. Furthermore, such compounds may also be used in the treatment of osteoporosis (WO 94/21242).

The compounds of formula (II) and, more particularly, the compounds of formulae (III) and (IV), their preparation and their therapeutic use have been described in French patent No. 2,623,498.

The compounds of formula (I) may be used for the preparation of the compounds of formula (II).

The compounds of formula (I) comprise a so-called asymmetric carbon which may have two configurations, R or S. They thus exist in the form of two enantiomers, which may be denoted by (I R) and (I S), according to the configuration of this asymmetric carbon:

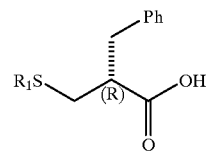
(IR)

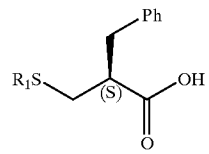
(IS)

No process of asymmetric synthesis of the derivatives of formula (I) has been described to date.

European patent No. EP 318,377 is known, in which the two enantiomers (I R) and (I S) of the acid of general formula (I) are obtained by separation of the racemic mixture using a chiral amine. However, this method of resolution makes it possible to obtain only a maximum of fifty (50) per cent of the desired enantiomer.

The aim of the present invention is to provide a process for the preparation of S-acyl derivatives of 2-mercaptomethyl-3-phenylpropanoic acid, in optically pure form.

Another aim of the invention is also to provide such a process which does not have the drawback of an optical separation as mentioned above.

The aim of the invention is also to provide a process for the preparation of optically active N-(mercaptoacyl)amino acid derivatives starting from S-acyl derivatives of 2-mercaptomethyl-3-phenylpropanoic acid.

To this end, the subject of the invention is a process for the asymmetric synthesis of S-acyl derivatives of 2-mercaptomethyl-3-phenylpropanoic acid of formula (I):

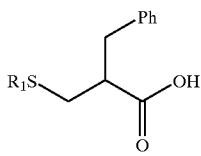
(I)

in which
R$_1$ represents a linear or branched aliphatic acyl radical or an aromatic acyl radical, characterized in that it comprises the steps consisting in:
a) preparing the diol of formula (VI):

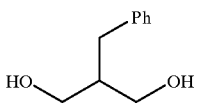
(VI)

by reduction of a malonic ester of formula (V):

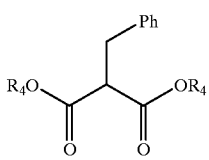
(V)

in which R$_4$ represents an alkyl chain containing from 1 to 4 carbon atoms, in the presence of a hydride;
b) preparing the monoacetate (VII) respectively of (R) configuration and of (S) configuration, of formulae (VII R) and (VII S):

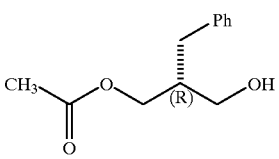
(VIIR)

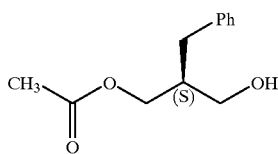
(VIIS)

c) subjecting the monoacetates of formula (VII R) or (VII S) to an oxidation in order to form the acids of formula (IX S) or (IX R):

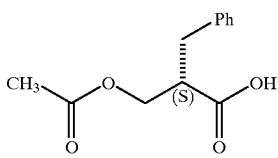
(IXS)

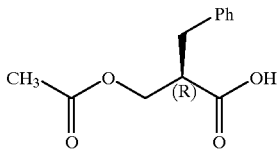
(IXR)

d) saponifying the compounds of formula (IX S) or (IX R), in the presence of a basic aqueous solution in order to form the hydroxy acids of formula (X S) or (X R):

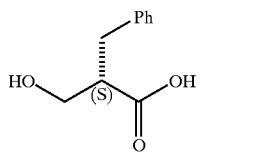
(XS)

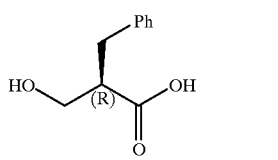
(XR)

e) thioacylating the hydroxy acids of formula (X S) or (X R) with a mercapto acid of formula (XI):

R$_1$SH (XI)

in which R$_1$ represents a linear or branched aliphatic acyl radical or an aromatic acyl radical, according to a reaction of Mitsunobu type in the presence of an alkyl azodicarboxylate/triphenylphosphine complex in order to lead respectively to the desired acids of formula (I R) or (I S):

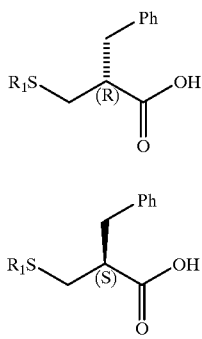

(IR)

(IS)

The subject of the invention is also a process for the preparation of optically active N-(mercapto-acyl) amino acid derivatives of formula (II):

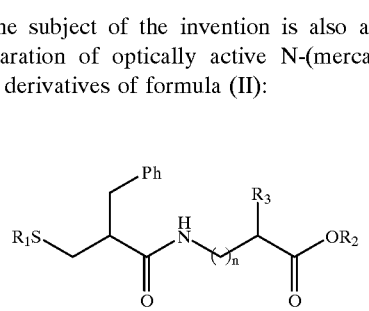

(II)

in which $R_1$ represents a hydrogen atom, a linear or branched aliphatic acyl radical or an aromatic acyl radical;

$R_2$ represents a lower alkyl radical, a phenyl radical or a lower phenylalkylene group;

$R_3$ represents a hydrogen atom; a lower alkyl group; a lower hydroxyalkylene group; a phenyl group; a lower phenylalkylene group; a lower hydroxyphenylalkylene group; a lower aminoalkylene group; a lower guanidinoalkylene group; a lower mercaptoalkylene group; a lower alkyl lower thioalkylene group; a lower imidazolylalkylene group; a lower indolylalkylene group; a lower carbamylalkylene group; a lower carboxyalkylene group; n ranges from 0 to 10;

characterized in that it comprises the use of S-acyl derivatives of 2-mercaptomethyl-3-phenylpropanoic acid of formula (I) in optically pure form as obtained according to the abovementioned process.

Lastly, the subject of the invention is also the use of S-acyl derivatives of 2-mercaptomethyl-3-phenylpropanoic acid of formula (I) in optically pure form as obtained by the abovementioned process, for the synthesis of optically active N-(mercaptoacyl) amino acid derivatives of formula (II) given above.

The Applicant has now found a process for the synthesis for the derivatives of formula (I) in optically pure form, which does not have the drawback of an optical separation.

According to an essential characteristic of the process in accordance with the invention, this process uses as starting material the benzylmalonic acid esters of formula (V):

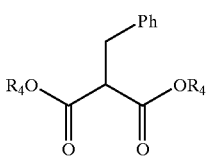

(V)

in which $R_4$ represents an alkyl chain containing from one to four carbon atoms.

The malonic esters of formula (V) are then reduced using a hydride, such as lithium aluminium hydride, to give the diol of formula (VI):

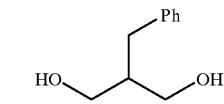

(VI)

Sodium borohydride may also be used.

The diol of formula (VI) is then monoacetylated using an enzyme, such as lipase PS (Amano) or the lipase obtained from Pseudomonas fluorescens (Fluka), in vinyl acetate in order to lead to the monoacetate (VII R) of (R) configuration:

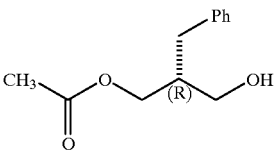

(VIIR)

In order to obtain the monoacetate of (S) configuration, the diol of formula (VI) is diacetylated either by the action of acetic anhydride in the presence of a catalyst such as, for example, a 4-dimethylaminopyridine/triethylamine or a sulphuric acid mixture, or using an enzyme such as Novozym 435 (Novo Nordisk) in vinyl acetate, in order to lead to the diacetate of formula (VIII):

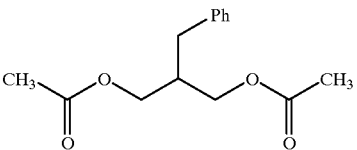

(VIII)

The diacetate of formula (VIII) is then monohydrolysed using an enzyme, such as lipase PS (Amano) or the lipase obtained from Pseudomonas fluorescens (Fluka), in aqueous medium, in order to lead to the monoacetate (VII S) of (S) configuration:

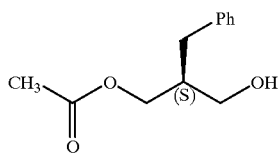

(VIIS)

The monoacetate of formula (VII R) or (VII S) is then oxidized using an oxidizing agent, such as Jones' reagent ($CrO_3$—$H_2SO_4$), in a solvent, such as acetone, in order to lead to the acid (IX S) of (S) configuration or to the acid of formula (IX R) of (R) configuration:

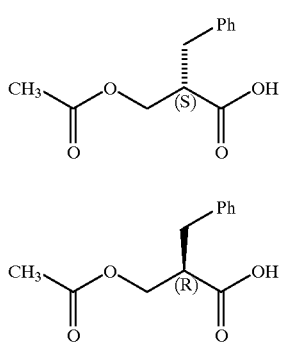

(IXS)

(IXR)

Potassium permanganate or nitric acid may also be used as oxidizing agent.

The compound of formula (IX S) or (IX R) is then saponified by an aqueous base solution, such as an aqueous sodium hydroxide solution or an aqueous lithium hydroxide solution, in order to lead to the hydroxy acid (X S) of (S) configuration or to the hydroxy acid (X R) of (R) configuration:

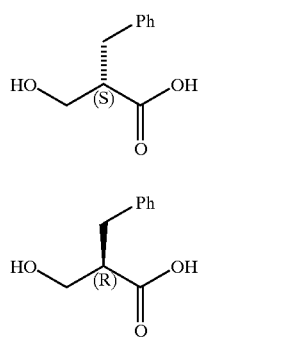

(XS)

(XR)

The enantioselective preparation of the monoacetates (VII S) and (VII R) and then of 2-substituted 3-hydroxypropionic acids with the aid of lipase P is known from publications K. Tsuji et al., Tetrahedron Lett., 30 (45), 6189–6192 (1989) and S. Atsuumi et al., Tetrahedron Lett., 31 (11), 1601–1604 (1990), these compounds serving as intermediates in the synthesis of renin inhibitors starting with 2-substituted 3-alkyl (or aryl) sulphonylpropionic acids.

The hydroxy acid of formula (X S) or (X R) is then thioacylated according to a reaction of Mitsunobu type (O. Mitsunobu, Synthesis, pp. 1–27, 1991) in the presence of an alkyl azodicarboxylate/triphenylphosphine complex and a mercapto acid of formula (XI):

$R_1SH$      (XI)

in which $R_1$ has the same meaning as in formula (I), in order to lead to the acids of formula (I R) of (R) configuration, or (I S) of (S) configuration.

The alkyl azodicarboxylate used for the Mitsunobu reaction is preferably chosen from diisopropyl azodicarboxylate or diethyl azodicarboxylate.

The mercapto acid (XI) used for the Mitsunobu reaction is preferably chosen from thioacetic acid and thiobenzoic acid.

The process in accordance with the invention is more particularly suitable for the preparation of (R)-2-acetylthiomethyl-3-phenylpropanoic acid of formula (Ia R) and (S)-2-acetylthiomethyl-3-phenylpropanoic acid of formula (Ia S), corresponding to the radical $R_1$=$CH_3CO$—:

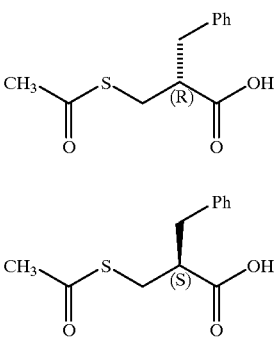

(IaR)

(IaS)

When applied to the synthesis of (R)-2-acetylthiomethyl-3-phenylpropanoic acid of formula (Ia R), the process in accordance with the invention comprises the steps consisting in:

a) reducing a malonic acid ester (V) such as dimethyl benzylmalonate ($R_4$=$CH_3$), using a hydride such as lithium aluminium hydride, in a solvent such as tetrahydrofuran, b) subjecting the diol (VI) formed to an enantioselective monoacetylation using an enzyme, such as lipase PS (Amano) or the lipase obtained from Pseudomonas fluorescens (Fluka), in a solvent such as vinyl acetate, c) oxidizing the monoacetate formed in the presence of an oxidizing agent, such as Jones' reagent in a solvent such as acetone, d) carrying out a saponification by an aqueous basic solution, such as an aqueous sodium hydroxide solution or a lithium hydroxide solution, followed by an acidification with an aqueous acid solution, for example an aqueous hydrochloric acid solution, in order to lead to the hydroxy acid of formula (XS):

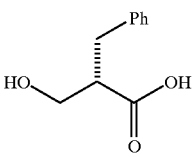

(XS)

g) and subjecting the hydroxy acid (XS) to a nucleophilic substitution reaction of Mitsunobu type in the presence, for example, of an alkyl azodicarboxylate/triphenylphosphine complex and thioacetic acid in a solvent such as tetrahydrofuran, in order to form the acid (Ia R).

When applied to the synthesis of (S)-2-acetylthiomethyl-3-phenylpropanoic acid of formula (Ia S), the process in accordance with the invention comprises the steps consisting in:

b) carrying out the diacetylation of the diol of formula (VI) either by the action of acetic anhydride in the presence of a catalyst such as, for example, a 4-dimethylaminopyridine/triethylamine or sulphuric acid mixture, or using an enzyme such as Novozym 435 (Novo Nordisk) in a solvent, for example vinyl acetate, subjecting the diacetate formed to an enantioselective mono-hydrolysis using an enzyme, such as lipase PS (Amano) or the lipase obtained from Pseudomonas fluorescens (Fluka), in a buffered medium, for example a 0.1 M pH 7 phosphate buffer and in an organic solvent such as acetone, c) oxidizing the monoacetate formed in the presence of an oxidizing agent, such as the Jones' reagent, in a solvent such as acetone, d) carrying out a saponification with an aqueous basic solution, such as an aqueous sodium hydroxide solution or an aqueous lithium hydroxide solution, followed by an acidification with an aqueous acidic solution, for example an aqueous hydrochloric acid solution, in order to lead to the hydroxy acid of formula (X R):

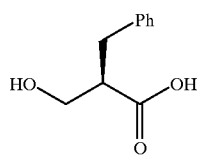

(XR)

e) and subjecting the hydroxy acid (X R) to a nucleophilic substitution reaction of Mitsunobu type in the presence, for example, of an alkyl azodicarboxylate/triphenylphosphine complex and thioacetic acid in a solvent such as tetrahydrofuran, in order to form the acid (Ia S).

The optically pure acids of formula (I S) of (S) configuration or (I R) of (R) configuration, obtained by the process in accordance with the present invention, find a particularly advantageous use in the synthesis of optically pure N-(mercaptoacyl)amino acids of formula (II).

They are particularly suitable for the synthesis of amino acid derivatives of formulae (III) and (IV).

The preparation of the N-(mercaptoacyl)amino acids from the acids of formula (I) is known and is described, for example, in European patent No. EP 501,870.

Thus, the N-(mercaptoacyl)amino acids may be obtained by the sequence of steps given below:

f) the acid of formula (I), in optically pure (I R) or (I S) form, is converted into acid chloride (XII S) or (XII R) using a chlorinating agent such as thionyl chloride or oxalyl chloride:

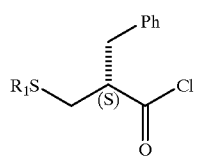

(XIIS)

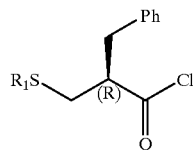

(XIIR)

$R_1$ having the same meaning as in formula (I), g) the acid chloride of formula (XII) in optically pure (XII S) or (XII R) form is then coupled with an amino ester of formula (XIII):

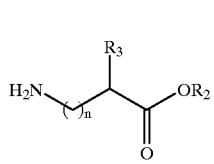

(XIII)

where
$R_2$, $R_3$ and n have the meanings which have been given in formula (II), in the presence of a base such as triethylamine, in order to form the optically pure derivatives of formula (II):

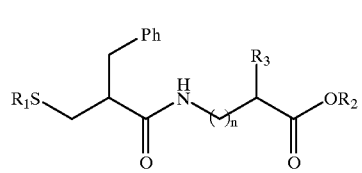

(II)

A few examples illustrating the use of the process in accordance with the invention will be given below, without any limitation being implied.

EXAMPLE 1

(R)-2-Acetylthiomethyl-3-phenylpropanoic acid (Ia R)

Stage a: 2-benzyl-1,3-propanediol (VI)

15 g (395.2 mmol) of lithium aluminium hydride are added to 200 ml of anhydrous tetrahydrofuran in a one-litre three-necked conical flask. A solution prepared from 22.5 g (101.3 mmol) of dimethyl benzylmalonate and 30 ml of anhydrous tetrahydrofuran is added with stirring so as to achieve a gentle reflux. The reaction medium is maintained at reflux for three hours. The mixture is cooled with an ice bath, diluted with 140 ml of tetrahydrofuran and hydrolysed by successive addition of 15 ml of water, 15 ml of aqueous 15% sodium hydroxide solution and 45 ml of water.

After stirring for 0.5 hour at room temperature, the reaction medium is milky white. The precipitate is filtered off and washed with 300 ml of ethyl ether. The organic phase is dried over magnesium sulphate, filtered and concentrated. 16 g of solid are obtained, which product is triturated from 200 ml of ice-cold petroleum ether. After filtration and drying under vacuum over $P_2O_5$, 15 g (90.24 mmol) of 2-benzyl-1,3-propanediol are obtained.

Mass=15 g
Yield=89%
Melting point=68° C. (Köfler)
IR $(cm^{-1})$: 3255

$^1$H NMR (CDCl$_3$): 7.4 to 7.0 (m, 5H); 3.9 to 3.5 (m, 4H); 3.1 (broad s, 2H); 2.55 (d, 2H, J=7 Hz); 2.1 to 1.9 (m, 1H).

$^{13}$C NMR (CDCl$_3$): 139.7; 128.9; 128.3; 126.0; 65.0; 43.7; 34.1.

Stage b: (R)-3-acetoxy-2-benzylpropanol (VII R)

10 mg of lipase PS (Amano) are added to a suspension of 4 g (24 mmol) of 2-benzyl-1,3-propanediol (stage a) in 40 ml of vinyl acetate and the mixture is stirred for 48 hours at this temperature. The reaction medium is filtered and concentrated.

(R)-3-Acetoxy-2-benzylpropanol acetate is thus obtained in the form of an oil.

Mass=4.29 g
Yield=86%
$[\alpha]_D^{20}$=+28.5° (CHCl$_3$, c=1.15)
IR (cm$^{-1}$): 1735
$^1$H NMR (CDCl$_3$): 7.35 to 7.10 (m, 5H); 4.25 to 4.0 (m, 2H); 3.65 to 3.40 (m, 2H); 2.75 to 2.50 (m, 2H); 2.20 to 2.0 (m, 2H); 2.05 (s, 3H).
$^{13}$C NMR (CDCl$_3$): 190.7; 138.1; 128.9; 128.4; 126.2; 63.6; 61.9; 42.5; 34.2; 20.8.

Stage c: (S)-2-benzyl-3-acetoxypropanoic acid (IX S)

22.8 ml of Jones' reagent are added dropwise, at 0° C., to 4.0 g (19.2 mmol) of (R)-3-acetoxy-2-benzylpropanol (VII R) above dissolved in 80 ml of acetone. The mixture is then stirred for 10 minutes at 0° C., after which 10 ml of isopropanol are added at this temperature. The stirring is continued for one hour at 0° C.

The reaction medium is filtered. The filtrate is diluted with 40 ml of water and then concentrated under vacuum in order to remove the acetone. The residue is basified under cold conditions (0, +10° C.) with sodium hydrogen carbonate to pH=9. The basic aqueous phase is then washed with ethyl acetate (three times 15 ml).

The aqueous phase is then cooled using an ice-water bath and acidified to pH=1 with concentrated hydrochloric acid solution.

The aqueous phase is extracted with ethyl acetate (three times 15 ml).

The extraction phases are combined, washed with water (10 ml once), dried over magnesium sulphate, filtered and concentrated under vacuum.

(S)-2-Benzyl-3-acetoxypropanoic acid (IX S) is thus obtained in the form of an oil.

Mass=2.8 g
Yield=65%
$[\alpha]_D^{20}$=+11.5° (CHCl$_3$, c=0.98)
IR (cm$^{-1}$): 2960, 1740, 1705
$^1$H NMR (CDCl$_3$): 10.4 (broad s, 1H); 7.35 to 7.1 (m, 5H); 4.3 to 4.15 (m, 2H); 3.15 to 2.95 (m, 2H); 2.95 to 2.75 (m, 1H); 2.05 (s, 3H).
$^{13}$C NMR (CDCl$_3$): 178.5; 170.6; 137.4; 128.7; 128.5; 126.7; 63.4; 46.1; 34.3; 20.8.

Stage d: (S)-2-benzyl-3-hydroxypropanoic acid (X S)

2.64 g (62.9 mmol) of lithium hydroxide monohydrate are added, at 0° C., to a solution of 3.52 g (15.84 mmol) of (S)-2-benzyl-3-acetoxypropanoic acid (IX S) and 35 ml of a mixture of tetrahydrofuran and water (75/25). The mixture is stirred for a further one hour at 0° C. It is acidified with 22 ml of aqueous 3M hydrochloric acid solution and then extracted with ethyl ether (50 ml once, 15 ml twice).

The ether phases are combined, dried over magnesium sulphate, filtered and concentrated under vacuum. The solid residue obtained is triturated at about 5° C. with petroleum ether. The mixture is filtered, drained and dried under vacuum.

Mass=2.45 g
Yield=86%
Melting point=63–65° C.
$[\alpha]_D^{20}$=14.3° (c=1.15 in chloroform)
IR (cm$^{-1}$): 1705
$^1$H NMR (CDCl$_3$): 7.4 to 7.1 (m, 5H); 5.85 (broad s, 2H); 3.85 to 3.6 (m, 2H); 3.15 to 2.95 (m, 1H); 2.95 to 2.75 (m, 2H).
$^{13}$C NMR (CDCl$_3$): 178.3; 138.2; 128.8; 128.5; 126.5; 61.9; 48.8; 33.9.
Optical purity ≧95%

Stage e: (R)-2-acetylthiomethyl-3-phenylpropanoic acid (Ia R)

2.44 g (12.05 mmol) of diisopropyl azodicarboxylate are added dropwise, at 0° C., to a solution of 3.16 g (12.05 mmol) of triphenylphosphine in 30 ml of tetrahydrofuran. Once the addition is complete, the mixture is stirred for 30 minutes at this temperature. The reaction medium is cooled to −10° C. and a solution of 1.45 g (8.05 mmol) of (S)-2-benzyl-3-hydroxypropionic acid (X S) and 0.92 g (12.05 mmol) of thioacetic acid in 10 ml of tetrahydrofuran is added dropwise. Once the addition is complete, the mixture is stirred for one hour at −10° C. and for a further two hours at room temperature.

The reaction medium is evaporated under vacuum and 25 ml of saturated aqueous sodium hydrogen carbonate solution are added, followed by 15 ml of ethyl acetate. After five minutes of vigorous stirring, the mixture is left to separate out by settling and the aqueous phase is collected. The organic phase is then reextracted with 20 ml of saturated aqueous sodium hydrogen carbonate solution. The basic aqueous phases are combined, washed with 10 ml of ethyl acetate and acidified to pH 1 with 3 ml of concentrated hydrochloric acid.

The acidic aqueous phase is then extracted with ethyl acetate (2×15 ml).

The organic phases are combined, dried over magnesium sulphate, filtered and concentrated under vacuum.

(R)-2-Acetylthiomethyl-3-phenylpropanoic acid (Ia R) is thus obtained in the form of an oil.

Mass=1.57 g
Yield=82%
$[\alpha]_D^{25}$=+33.7° (CH$_3$OH, c=0.98)
IR (cm$^{-1}$): 1700
$^1$H NMR (CDCl$_3$): 9.5 (broad s, 1H); 7.40 to 7.10 (m, 5H); 3.20 to 2.80 (m, 5H); 2.30 (s, 3H).
$^{13}$C NMR (CDCl$_3$): 195.1; 179.3; 137.3; 128.8; 128.4; 126.6; 46.8; 37.3; 30.3; 29.4.
ee≧95%

* Optical purification in order to obtain (R)-2-acetylthiomethyl-3-phenylpropanoic acid (Ia R)

1.54 g (6.5 mmol) of (R)-2-acetylthiomethyl-3-phenylpropanoic acid (Ia R) above and 15.4 ml of ethyl ether are placed in a 50 ml round-bottomed flask. The mixture is stirred until dissolution is complete and 1.07 g (6.5 mmol) of D(+)-epherdrine are then added at room temperature. The mixture is stirred for one hour at room temperature. It is filtered and the product is drained, washed with 5 ml of ice-cold ethyl ether and dried under vacuum. A white salt is obtained.

Mass=2.41 g
Yield=92%
$[\alpha]_D^{20}$=+48.4° (CH$_3$OH, c=0.95)

The above (+)-ephedrine salt is then suspended in 10 ml of ethyl ether. 9 ml of aqueous 1N hydrochloric acid aqueous solution are added and the mixture is stirred vigorously until the salt has dissolved.

The mixture is left to separate out by settling and the ether phase is collected. The organic phase is dried over magnesium sulphate, filtered and concentrated under vacuum. Optically pure (R)-2-acetylthiomethyl-3-phenylpropanoic acid (Ia R) is thus obtained in the form of an oil.

Mass=1.37 g
Yield=89%
$[\alpha]_D^{25} 35.7°$ (CH$_3$OH, c=1.3)

EXAMPLE 2

(S)-2-Acetylthiomethyl-3-phenylpropanoic acid (Ia S)

Stage a: 2-benzyl-1,3-propanediol diacetate (VIII)

100 mg of Novozym 435 enzyme are added to a suspension of 1.89 g (11.37 mmol) of 2-benzyl-1,3-propanediol (VI) in 10 ml of vinyl acetate at 29° C. and the mixture is stirred for 24 hours at this temperature. The reaction medium is filtered and concentrated.

The 2-benzyl-1,3-propanediol diacetate (VIII) is thus obtained in the form of an oil.

Mass=2.79 g
Yield=98%
$^1$H NMR (CDCl$_3$): 7.35 to 7.10 (m, 5H); 4.15 to 3.90 (m, 4H); 2.75 to 2.60 (m, 2H); 2.40 to 2.25 (m, 1H); 2.05 (s, 6H).

Stage b: (S)-3-Acetoxy-2-benzylpropanol (VII S)

130 mg of lipase obtained from Pseudomonas fluorescens (Fluka) are added to 0.25 g (1 mmol) of 2-benzyl-1,3-propanediol diacetate (VIII) above dissolved in a mixture of 9.9 ml of acetone and 23.1 ml of phosphate buffer pH=7, and the medium is then heated at 30° C. for 48 hours. The solution is then extracted with ethyl ether (twice 20 ml). The ether phases are combined, dried over magnesium sulphate, filtered and concentrated under vacuum. The residue is purified by chromatography on silica (7/3 ethyl ether/petroleum ether eluent). 80 mg of oil are obtained.

Yield=38%
$[\alpha]_D^{20}$=27.1° (c=1.04 in chloroform)

The spectral characteristics are identical to those of compound (VII R) (Example 1, stage b).

Stage c: (R)-2-benzyl-3-acetoxypropanoic acid (IX R)

The above acetate (VII S) is oxidized to the acid according to the same procedure as that described in Example 1, stage c.

Yield=68%
$[\alpha]_D^{20}$=−11.3° (c=1.0 in chloroform)

Stage d: (R)-2-Benzyl-3-hydroxypropanoic acid (X R)

The product of stage c above is treated with aqueous lithium hydroxide solution as described in Example 1, stage d.

Yield=91%
$[\alpha]_D^{0}$=+14.1° (c=1.12 in chloroform)
Optical purity ≧95%

Stage e: (S)-2-acetylthiomethyl-3-phenylpropanoic acid (Ia S)

The above hydroxy acid is substituted with thioacetic acid in a Mitsunobu-type reaction, using the same procedure as that described in Example 1, stage e in order to lead to (S)-2-acetylthiomethyl-3-phenylpropanoic acid (Ia S).
ee≧95%

Yield after treatment with (−)-epherdrine=70%
$[\alpha]_D^{25}$=−34.8° (c=1.1 in methanol)

EXAMPLE 3

Benzyl N—(R)-[2-acetylthiomethyl-1-oxo-3-phenylpropyl]glycinate (III)

Stage f: 2-acetylthiomethyl-3-phenylpropanoyl chloride (XII S)

2.0 g (8.40 mmol) of (R)-2-acetylthiomethyl-3-phenylpropanoic acid (Ia R) (Example 1, stage e) are placed in a round-bottomed flask. The flask is cooled by an ice-water bath and 1.2 g (10.08 mmol) of thionyl chloride are added dropwise. The mixture is stirred overnight to room temperature.

The excess thionyl chloride is evaporated off on a rotary evaporator. 2.15 g of a yellowish oil are obtained.

Quantitative yield
$[\alpha]_D^{25}$=+29.9° (c=1.20 in chloroform)
IR (cm$^{-1}$): 1790 to 1780, 1695 to 1685
$^1$H NMR (CDCl$_3$): 7.4 to 7.1 (m, 5H); 3.5 to 2.8 (m, 5H); 2.25 (s, 3H).

Stage g: benzyl N—(R)-[2-acetylthiomethyl-1-oxo-3-phenylpropyl]glycinate (III)

2.83 g (8.40 mmol) of benzyl glycinate in the form of the para-toluenesulphonate salt in 6 ml of dichloromethane are placed in a three-necked flask fitted with a calcium chloride guard tube. The flask is cooled to 5° C. by an ice-water bath.

A solution of 1.70 g (16.83 mmol) of triethylamine in 5 ml of dichloromethane is added dropwise at a temperature of between 5 and 15° C. The mixture is stirred for 10 minutes and a solution of 2.15 g (8.40 mmol) of the above acid chloride in 5 ml of dichloromethane is then added without exceeding 15° C. in the medium.

The mixture is allowed to return to room temperature and is then stirred for a further three hours.

The reaction medium is washed with water (5 ml once), with aqueous normal hydrochloric acid solution (5 ml once), with saturated aqueous sodium hydrogen carbonate solution (5 ml once) and with saturated aqueous sodium chloride solution (5 ml once).

The organic phase is dried over magnesium sulphate, filtered and concentrated under vacuum. 3.2 g of a solid residue are obtained, which product is dissolved in hot isopropanol (12 ml).

The solution is filtered while hot. The filtrate is cooled with an ice-water bath. The solid is filtered off, washed with diisopropyl ether, drained and dried under vacuum over phosphorus pentoxide.

Mass obtained=2.1 g
Yield=65%
Melting point=69° C.
$[\alpha]_D^{20}$=+24.5° (c=1.0 in methanol)
IR (nujol) (cm$^{-1}$): 3280, 1755, 1695, 1640
$^1$H NMR (CDCl$_3$): 7.40 to 7.10 (m, 10H); 6.15 (broad t, 1H); 5.25 (s, 2H); 4.10 to 3.5 (split AB, 2H); 3.10 to 2.55 (m, 5H); 2.30 (s, 3H).
$^{13}$C NMR (CDCl$_3$): 195.8; 172.9; 169.2; 138.4; 135,0; 128,7; 128.4; 128.2; 126.5; 66.9; 49.1; 41.2; 38.2; 31.0; 30.4.

Elemental analysis C$_{21}$H$_{23}$O$_4$NS

|  | C | N | H |
|---|---|---|---|
| % calculated | 65.45 | 3.63 | 5.97 |
| % found | 65.34 | 3.95 | 6.10 |

EXAMPLE 4

Benzyl N—(S)-[2-acetylthiomethyl-1-oxo-3-phenylpropyl]glycinate (IV)

Stage f: 2-acetylthiomethyl-3-phenylpropanoyl chloride (XII R)

(S)-2-Acetylthiomethyl-3-phenylpropanoic acid (Ia S) (Example 2, stage e) is treated with thionyl chloride according to the same procedure as that described in Example 3, stage f.

Quantitative yield $[\alpha]_D^{25} = -30.1°$ (c=1.37 in chloroform)

Stage g: benzyl N—(S)-[2-acetylthiomethyl-1-oxo-3-phenylpropyl]glycinate (IV)

The above acid chloride is coupled with benzyl glycinate according to the same procedure as that described in Example 3, stage g.

Yield=66%

$[\alpha]_D^{20} = -24.9°$ (c=1.0 in methanol)

Elemental analysis: $C_{21}H_{23}O_4NS$

|  | C | N | H |
|---|---|---|---|
| % calculated | 65.45 | 3.63 | 5.97 |
| % found | 65.02 | 3.88 | 5.87 |

We claim:

1. A process for the preparation of an S-acyl of the formula

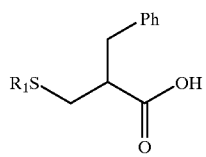

I wherein $R_1$ is an acyl of an aliphatic carboxylic acid or an aromatic carboxylic acid and Ph is phenyl comprising (a) reducing a malonic acid ester of the formula

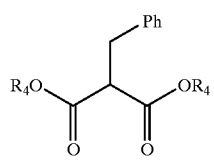

V wherein $R_4$ is alkyl of 1 to 4 carbon atoms in the presence of a hydride to obtain a diol of the formula

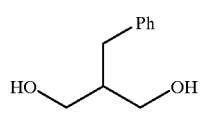

VI b) reacting the compound of Formula VI with an acetylating agent to obtain the monoacetates of the formula

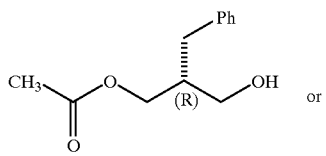

VIIR or

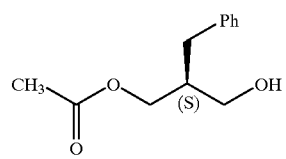

VIIS c) oxidizing the monoacetates of formula (VIIR) or (VIIS) to form the acids of the formulae

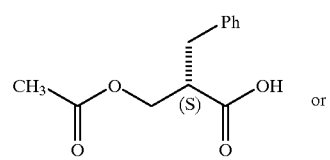

IXS or

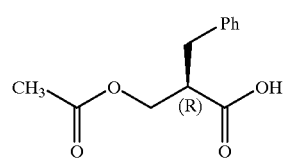

IXR d) saponifying the compounds of formula IXS and IXR in the presence of a basic aqueous solution to form the hydroxy acids of the formulae

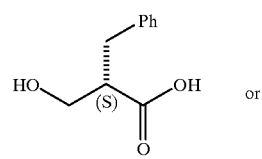

XS or

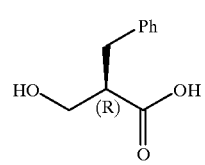

XR e) thioacylating the said hydroxy XS and XR acids with a mercapto acid of the formula

R₁SH            XI wherein $R_1$ is aliphatic acyl or an aromatic acyl as defined above, according to a reaction of Mitsunobu type in the presence of an alkyl azodicarboxylate/triphenylphosphine complex to obtain the desired acids of the formulae

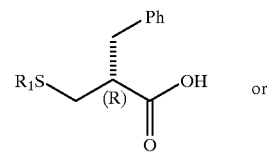

IR or

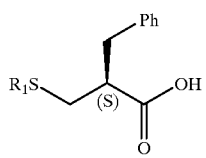

2. The process of claim 1 wherein the acetylating agent is vinyl acetate in the presence of an enzyme.

3. The process of claim 1 wherein the monoacetate (VIIS) of S configuration is obtained by preparation of the diacetate of formula (VIII):

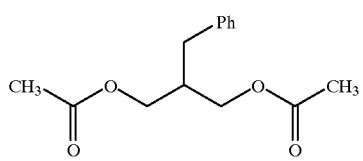

from the diol of formula (VI) and then by enantioselective monohydrolysis of the diacetate of formula (VIII) in the presence of an enzyme, to form the monoacetate derivative.

4. The process of claim 3 wherein the diacetate of formula (VIII) is obtained by reacting the diol of formula (VI) with acetic anhydride in the presence of a catalyst.

5. The process of claim 3 wherein the diacetate of formula (VIII) is obtained by reacting the diol of formula (VI) with vinyl acetate in the presence of an enzyme.

6. The process of claim 1 wherein the hydride used in step a) is lithium aluminum hydride or sodium borohydride.

7. The process of claim 2 wherein the enzyme used in step b) is lipase PS or lipase obtained from Pseudomonas fluorescens.

8. The process of claim 4 wherein the catalyst used in step b) is a mixture of 4-dimethylaminopyridine/triethylamine and sulfuric acid.

9. The process of claim 3 wherein the enzyme used in step b) is Novozym 435.

10. The process of claim 3 wherein the enzyme used in step b) is the lipase obtained from Pseudomonas fluorescens or lipase PS.

11. The process of claim 1 wherein the oxidizing agent used in step (c) is Jones' reagent or potassium permanganate or nitric acid.

12. The process of claim 1 wherein the aqueous basic solution used in step d) is an aqueous lithium hydroxide solution or an aqueous sodium hydroxide solution.

13. The process of claim 1 wherein the alkyl azodicarboxylate used in step e) is diisopropyl azodicarboxylate or diethyl azodicarboxylate.

14. The process of claim 1 wherein the mercapto acid of formula (XI) used in step e) is thioacetic acid or thiobenzoic acid.

15. The process of claim 1 for the preparation of (R)-2-acetylthiomethyl-3-phenylpropanoic acid of the formula

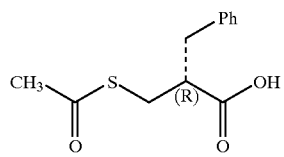

comprising a) reducing dimethyl benzylmalonate with lithium aluminum hydride in tetrahydrofuran to obtain the corresponding diol (VI);

b) carrying out a monoacetylation of the diol of formula (VI) with vinyl acetate, in the presence of lipase PS Amano, c) oxidizing the alcohol function of the monoacetate of formula (VIIR) thus obtained, in acetone, using Jones' reagent (CrO$_3$—H$_2$SO$_4$)

d) saponifying the acetate function with an aqueous lithium hydroxide solution, and then liberating, by acidification, the hydroxy acid of the formula

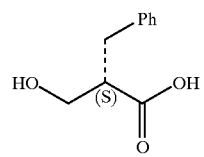

and e) substituting the alcohol function of the hydroxy acid of formula (XS) according to a Mitsunobu-type reaction in the presence of a triphenylphosphine/diisopropyl azodicarboxylate complex and thioacetic acid to obtain the acid of (R) configuration of formula (IaR).

16. The process of claim 53 for the preparation of (S)-2-acetylthiomethyl-3-phenylpropanoic acid of the formula

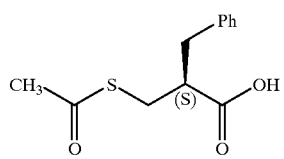

comprising a) reducing dimethyl benzylmalonate with lithium aluminum hydride, b) carrying out a diacetylation of the diol of formula (VI) with vinyl acetate in the presence of enzyme Novozym 435 and then carrying out a mono-hydrolysis of the diacetate of formula (VIII) thus formed in a pH7 phosphate buffer, in the presence of lipase obtained from Pseudomonas fluorescens, c) oxidizing the monoacetate of formula (VIIS) in acetone, using Jones' reagent (CrO$_3$—H$_2$SO$_4$), d) saponifying the acetate function with an aqueous lithium hydroxide solution, and then liberating, by acidification, the hydroxy acid of formula

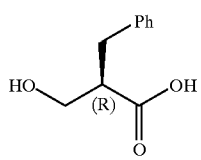

and e) substituting the alcohol function of the hydroxy acid of formula (XR) according to a Mitsunobu-type reaction in the presence of a triphenylphosphine/diisopropyl azodicarboxylate complex and thioacetic acid to obtain the acid of (S) configuration of formula (IaS).

17. The process for the preparation of optically active N-(mercaptoacyl)amino acid derivatives of the formula

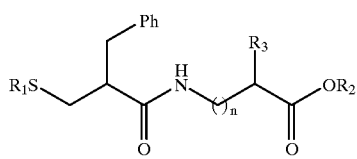

wherein $R_1$ is selected from the group consisting of hydrogen, aliphatic acyl of a carboxylic acid and aromatic acyl of a carboxylic acid, $R_2$ is selected from the group consisting of hydrogen, alkyl of 1 to 4 carbon atoms, phenyl and lower phenylalkylene, $R_3$ is selected from the group consisting of hydrogen, lower alkyl, lower hydroxyalkylene, phenyl, lower phenylalkylene, lower hydroxyphenylalkylene, lower aminoalkylene, lower guanidinoalkylene, lower mercaptoalkylene, lower alkyl, lower thioalkylene, lower imidazolylalkylene, lower indolylalkylene, lower carbamylalkylene and lower carboxyalkylene; and n is an integer from 0 to 10 comprising reacting a 2-mercaptomethyl-3-phenylpropanoic acid of formula (I) in optically pure form of claim 1 with a chlorinating agent to form the corresponding acid chloride of the formula

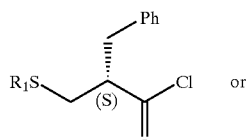 or

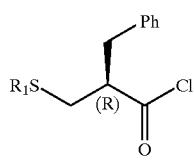

wherein $R_1$ has the definition of claim 1 and reacting the formulae XIIS and XIIR in the presence of a base with an amino ester of the formula

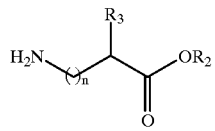

wherein $R_2$, $R_3$ and n have the above definition to obtain an optically pure compound of the formula

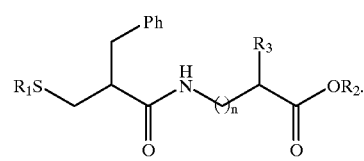

18. The process of claim 17 wherein the chlorinating agent is thionyl chloride or oxalyl chloride.

19. The process of claim 17 wherein the base is triethylamine.

20. The process of claim 17 for the preparation of benzyl N—(R)-[2-acetylthiomethyl-1-oxo-3-phenylpropyl]glycinate of the formula

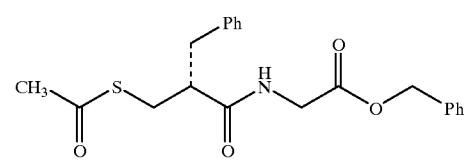

comprising reacting (R)-2-acetylthiomethyl 3-phenylpropanoic acid (IaR) of claim 15 with a chlorinating agent to form the corresponding acid chloride of the formula (XII S) and reacting the said acid chloride in the presence of a base with benzyl glycinate to obtain optically pure compound of formula (III).

21. The process of claim 17 for the preparation of benzyl N—(S)-[2-acetylthiomethyl-1-oxo-3-phenylpropyl]glycinate of the formula

IV

CH₃—S—...—N—...—O—Ph comprising reacting (S)-2-acetylthiomethyl-3-phenylpropanoic acid (IaS) of claim 16 with a chlorinating agent to form the corresponding acid chloride of the formula (XII R) and reacting the said acid chloride in the presence of a base with benzyl glycinate to obtain optically pure compound of formula (IV).

* * * * *